United States Patent [19]

Matsuzawa et al.

[11] Patent Number: 5,374,533
[45] Date of Patent: Dec. 20, 1994

[54] METHOD FOR DETERMINING CHONDROCALCIN

[75] Inventors: Kimihiko Matsuzawa; Kazuhiko Itou, both of Iwakuni; Hitomi Honda, Hino; Ryoichi Hasegwwa; Naomi Okamoto, both of Iwakuni; Kenji Hosoda, Kawagoe; Masayuki Shinmei, Tokorozawa; Shigeo Matsuyama, Wako, all of Japan

[73] Assignee: Tetjin Limited, Osaka, Japan

[21] Appl. No.: 51,266

[22] Filed: Apr. 23, 1993

Related U.S. Application Data

[63] Continuation of Ser. No. 455,329, Jan. 10, 1990, abandoned.

[30] Foreign Application Priority Data

May 10, 1988 [JP] Japan .................. 63-111402
Aug. 9, 1988 [JP] Japan .................. 63-197094
Aug. 10, 1988 [JP] Japan .................. 63-197877

[51] Int. Cl.$^5$ .................. G01N 33/53; G01N 33/553; G01N 33/543
[52] U.S. Cl. .................. 435/7.94; 435/7.9; 435/7.92; 435/810; 436/518; 436/525; 436/512; 436/811; 436/815; 530/388.85; 530/389.3
[58] Field of Search .................. 435/7.94, 7.9, 7.92, 435/810; 436/525, 518, 543, 811, 815, 512; 530/388.25, 389.3

[56] References Cited

FOREIGN PATENT DOCUMENTS 0138222 4/1985 European Pat. Off. .
0205337 12/1986 European Pat. Off. .
62-116262 5/1987 Japan .

OTHER PUBLICATIONS

Choi, H. V., et al., J. Biol. Chem., vol. 258, No. 1, pp. 655–661 (1983).
E. Livne et al., "Age-related changes in the role of matrix vesicles in the Mandibular Condylar Cartilage" J. Anat.; vol. 150; pp. 61–74; 1987.
A. Hinek et al., "The Calculation of Cartilage Matrix in Chondrocyte Culture: Studies of the C-Propetule of Type II Collagen (Chondrocalcin)"; The Journal of Cell Biology; vol. 104; pp. 1435–1441; May 1987.
A. R. Poole; "Association of an Extracellular Protein (Chondrocalcin) with the Calcification of Cartilage in Endochondral Bone Formation" The Journal of Cell Biology; vol. 98: pp. 54–65: Jan. 1984.
Kuroki et al., "Two-Site 'Simultaneous' Immunoassay with Monoclonal Antibodies for the Determination of Surfactant Apoproteins in Human Amniotic Fluid," Pediatric Research, vol. 19, No. 10, pp. 1017–1020 (1985).
Vogt, Jr. et al., "Quantitative Differences Among Various Proteins as Blocking Agents for ELISA Microtiter Plates," Journal of Immunological Methods, vol. 101, pp. 43–50 (1987).

Primary Examiner—Toni R. Scheiner
Attorney, Agent, or Firm—Sughrue, Mion, Zinn, Macpeak & Seas

[57] ABSTRACT

A method for determining chondrocalcin through an immunoassay using an enzyme(s)-labeled mammalian chondrocalcin or enzyme(s)-labeled anti-chondrocalcin antibody which is characterized by that mammalian body fluid is used as a specimen and immunoreaction in a solution is utilized to determine the chondrocalcin of the mammalian, reagents and a kit therefor.

This determination can be utilized for diagnosis or the like for cartilage-relating diseases in mammals.

15 Claims, 6 Drawing Sheets

METHOD FOR DETERMINING CHONDROCALCIN

This is a continuation of application Ser. No. 07/455,329 filed on Jan. 10, 1990 now abandoned.

FIELD OF THE ART

The present invention relates to a method for determining chondrocalcin according to the immunoassay using an enzyme(s)-labeled mammalian chondrocalcin or enzyme(s)-labeled anti-chondrocalcin antibody, which is characterized by using a body fluid of mammals is used as a specimen and the chondrocalcin of the mammals is determined utilizing the immunoreactions in the fluid.

Moreover, the present invention relates to a reagent for determination and a kit therefor.

Chondrocalcin is a protein isolated from epiphyseal cartilage of fetal bovine in 1983 for the first time by H. U. Choi et al, and has been known to be a molecule having a molecular weight of 69,000 and consisting of two subunits having a molecular weight of 35,000 [see H. U. Choi, et al., *J. Biol. Chem.* 258, 655–661, (1983)]. Subsequently, the chondrocalcin was identified to be C-propeptide of type II collagen by analysis of partial sequence of the amino acids [see M. V. D. Rest, et al., *Biochem. J.*, 237, 923–925 (1986)]. A histochemical study has been made on the distribution of the protein in a living body using bovines [see A. R. Poole et al., *J. Cell Biol.*, 98, 54–65 (1984); *Clinical Orthopaedics and Related Research*, 208, 114–118 (1986)]. According to this study, the protein mostly distributed in cartilage where calcification is advancing, especially in the hypertrophic zone of the growth plate, while scarcely in mature bones, teeth and other tissues.

The physiological action of this protein is presumed to participate closely in the calcification of cartilage, from the characteristic distribution in a living body and the fact that the protein binds to calcium ion and hydroxyapatite. In the course of these histochemical studies, immunological methods such as tissue staining have been applied and a polyclonal antibody obtained by immunizing a rabbit with bovine chondrocalcin has been employed to study bovine tissues.

In the meantime, there are few reports on the pathological study of chondrocalcin and future development can be expected. A. R. Poole et al. described that attention is being directed to chondrocalcin in connection with the pathology in the diseases relating to development, ossification of cartilage and abnormal calcification [see A. R. Pool et al., *Clinical Orthopaedics and Related Research* 208, 114–118 (1986)]. Therefore, the determination of chondrocalcin will play very important and significant roles in the basic medical and clinical studies on chondrocalcin.

A. Hinek et al. determined chondrocalcin in the cartilage extracts and supernatants of chondrocyte culture mixtures by the radioimmunoassay [A. Hinek et al., *J. Cell. Biol.* 104, 1435–1441 (1987)]. The lowest limit of this measurement was, however, 100 ng per ml specimen and the sensitivity was not enough to determine chondrocalcin in body fluid such as blood or synovial fluid. Moreover, the measurement of only extracts of cartilages with 4M guanidine hydrochloride aqueous solution (at 5.8 pH) and supernatants of chondrocyte culture in the DME medium were described, but not the measurement of the body fluid containing the factors which would inhibit the specific reactions or induce nonspecific reactions.

Accordingly, the development of high-sensitivity measurement of chondrocalcin which can determine chondrocalcin in body fluid, and the reagents and kits for the measurement is very important to the diagnosis of diseases, and monitoring treatment from clinical point of view.

The immunoassay based on antigen-antibody reactions utilizes the specific reaction between an antigen and an antibody in body fluid containing many components. Actually, however, nonspecific reactions other than the target antigen-antibody reaction occur and inhibitory reactions, when body fluid is used as a specimen. Thus, when a known amount of an antigen to be measured is added to the specimen, the exact amount sometimes cannot be determined or the sensitivity necessary for measuring the antigen cannot be obtained. The causes of reactions other than the specific one are not always elucidated thoroughly, but it is understood that these reactions occur, when compounds having antigenicity similar to that of the target substance are present, or in case of the presence of substances such as rheumatoid factor reacting with the Fc moiety of IgG, known as non-specific antibody. In laboratory examinations, therefore, the exact measurement of the target substance in body fluid is always an extremely important subject matter.

The present inventors have resolved the above-stated problems and achieved the invention which can determine chondrocalcin in body fluid.

DISCLOSURE OF THE INVENTION

The present invention is a method for determining chondrocalcin according an immunoassay using enzyme(s)-labeled mammalian chondrocalcin or anti-chondrocalcin antibody, which is characterized by that the use of mammalian body fluid as a specimen and the chondrocalcin of mammalian animals is determined utilizing immunoreactions in solutions.

Moreover, the present invention is a reagent for determining chondrocalcin in mammalian body fluid as a specimen, which is composed of an anti-chodrocalcin antibody reagent immobilized on an insoluble support and an anti-chondro-calcin antibody reagent labeled with an enzyme, and a kit for determining chondrocalcin in mammalian body fluid immunologically, which is composed of an anti-chondrocalcin antibody immobilized on an insoluble support, a labeled anti-chondrocalcin antibody, a solubilizer, a washing agent, a substrate for measuring the enzyme activity and a reaction terminator for the enzyme.

Moreover, the present invention is a monoclonal antibody which is characterized by recognition of mammalian chondrocalcin.

BRIEF EXPLANATION OF THE DRAWINGS

In FIG. 6, black dots and white dots give 5 ng/ml and 0 ng/ml of final chondrocalcin concentrations, respectively.

BEST EMBODIMENT OF THE INVENTION

Figure 1:
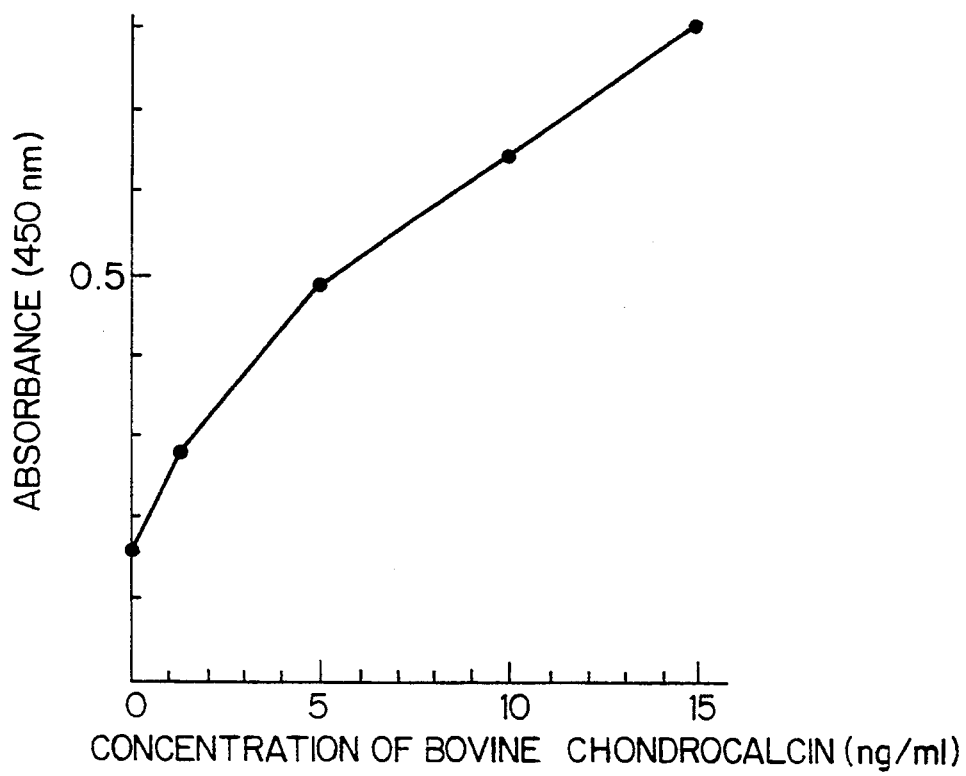
FIG. 1 is a calibration curve for bovine chondrocalcin using a monoclonal antibody "Chon-5G" and another monoclonal antibody labeled with HRP "Chon-8G" as reagents for determination.

In the first place, the reagents for determining chondrocalcin according to the present invention will be described. The reagents according to the present invention comprise one reagent of anti-chondrocalcin antibody immobilized to an insoluble support and the other reagent of anti-chondrocalcin antibody labeled with an enzyme wherein such anti-chondrocalcin antibody is, for example, anti-chondrocalcin polyclonal antibody, or anti-chondrocalcin monoclonal antibody.

The chondrocalcin as an antigen for obtaining the polyclonal antibody used in the present invention is in principle of a natural type extracted from a natural substance, but may be of other types obtained, for example, through protein engineering or biotechnology, as long as the chondrocalcins are immunologically equivalent to natural ones such as a hapten, namely the peptide containing the antigen determinants of the natural chondrocalcin.

Material for obtaining chondrocalcin of the natural type, includes, for example, cartilage of mammalian fetuses and those of mammals at the growing stage, and the cartilages of bovine fetus are preferred, because they are available with relative easiness. The isolation and purification can be done by a combination of usual techniques for protein isolation such as salting-out, extraction, centrifugation, ultrafiltration, a variety of chromatography, and the method described by H. U. Choi is one of the examples.

The monoclonal antibody is prepared by culturing a hybridoma formed by the cell fusion technique according to G. Koeller and Milstein [*Nature* (London), 256, 495–497 (1975)] and isolating from the culture mixture containing the antibody excreted. In other words, a mouse is immunized with a chondrocalcin originating from a mammalian animal, and the mouse lymphocytes are fused with the mouse myeloma cells to give hybridomas. As the hybridomas given by this process produce a variety of monoclonal antibodies, the hybridoma producing the target monoclonal antibody is cloned whereby cloned hybridoma is isolated. The cloned hybridoma is cultured in vitro to excrete the monoclonal antibody. Anti-chondrocalcin antibody is separated from the supernatant of the culture mixture.

The polyclonal antibody is obtained through a usual process, for example, by a method described in the lecture course using *Experimental Biochemistry*, Vol. 5, pages 1 to 10, 2nd series, edited by the Biochemical Society of Japan, published by Tokyo Kagaku Dojin Co. Ltd. (Japan) (1986).

The animal to be immunized is not particularly limited, as long as it is a different mammal from the one from which chondrocalcin was obtained as an antigen. For example, when bovine chondrocalcin is used as an antigen, sheep, rabbits, Guinea pigs, rats or mice are preferably used.

When articular cartilage of human fetus and of normal adult were tissue-stained with the anti-bovine-chondrocalcin polyclonal antibody and the monoclonal antibody, the former gave tinted image but the latter did not. This result evidently shows that the antibody according to the present invention recognizes human chondrocalcin.

In the present invention, the above-stated polyclonal antibody or monoclonal antibody is used at least in a labeled anti-chondrocalcin antibody. Additionally, when the anti-chondrocalcin antibody immobilized to an insoluble support or to be immobilized to an insoluble support is used, the combination can be selected from cases where both are polyclonal antibodies, both are monoclonal antibodies, and one antibody is polyclonal and the other is monoclonal.

In some cases, Fab', F(ab') or Facb fragments are preferred as the labeled antibody. In other words, first, there exists components bonding to the Fc moiety of the antibody such as the rheumatoid factor and such components cause reactions with nonspecific antibodies other than the target antigen-antibody reaction. Consequently, exact determination of chondrocalcin in body fluid becomes difficult. When the fragment is used as the labeled antibody, however, these reactions do not occur and exact values are given. Secondly, in order to obtain sensitivity sufficient to satisfactorily measure chondrocalcin in specimens of body fluid, it is required that nonspecific reactions to the insoluble support are reduced as much as possible, and the labeled fragment is preferably used as the labeled antibody, because these nonspecific reactions are inhibited.

Such fragment is obtained, in case of F(ab')$_2$ or Fab', by hydrolyzing the polyclonal or monoclonal antibody through a known procedure, for example, hydrolyzing with pepsin, or further subjecting F(ab')2 fragment to reductive treatment to convert into Fab' fragment [see, for example, A. Nisonoff et al. *Arch. Biochemo Biophys.*, 89, 230 (1960): P. Parham., *J. Immunoi.*, 131, 2895 (1983)].

Radioisotopes have been well known as a labeling substance, but their use is limited in industrial production, because they may cause pollution, and have use time limitations and, further, the operators are required to, undergo special training. Thus, enzymes are suitable for this purpose, because they have amplifying action without the defects of radioisotopes.

Enzymes bonding to anti-chondrocalcin antibody, include, for example, lysozyme, maleate dehydrogenase, glucoe-6-phosphate dehydrogenase, peroxidase, glucose oxidase, alkali phosphatase, luciferase, $\beta$-galactosidase, alcohol dehydrogenase, and invertase.

These enzymes are bonded to the anti-chondrocalcin antibody by a usual method such as the glutaraldehyde method, the periodate method or the maleimide method. For example, a maleimidized antibody or fragment of the antibody is allowed to react with a thiolated enzyme in a solvent. Maleimidization of an antibody or antibody fragment can be done using, for example, succinimidyl 4-(N-maleimidemethyl)cyclohexane carbonate (SMCC), sulfosuccinimidyl 4-(N-maleimidemethyl)-cyclohexane carbonate (sulfoSMCC), succinimidyl-m-maleimidebenzoate (MBS), and succinimidyl 6-maleimide hexanoate (EMCS).

The introduction of mercapto groups into enzymes can be accomplish by a known method, (for example, see *Enzyme Immunoassay*; edited by Ishikawa (Igakushoin) in Japanese). For example, it can be done by allowing an enzyme to react with S-acetylmercaptosuccinic anhydride (AMSA) or N-succinimidyl-3-(2-pyridylthiopropionate (SPDP).

The labeling number of the enzyme in the bonded antibody obtained from an enzyme and anti-chondrocalcin antibody, namely in an enzyme(s)-labeled antibody can be determined by measurement of molecular weight, absorbance or enzyme activity. For example, when the enzyme is peroxidase, the absorbance at 280 nm wavelength originating from the antibody and peroxidase and the absorbance at 403 nm originating from peroxidase are measured to determine the labeling number (E. Ishikawa et al., *J. Immunoassay.*, 4, 209–327 (1983), see page 243).

In other words, at 403 nm wavelength, there is no absorbance caused by the antibody and only by peroxidase, thus the concentration of peroxidase is calculated from the absorbance. Since the absorbance at 280 nm originates from both the antibody and peroxidase, the concentration of the antibody is calculated from the value subtracting the contribution of the peroxidase at 280 nm which is calculated from the concentration of peroxidase calculated from the absorbance at 403 nm and the molecular extinction coefficient of peroxidase at 280 nm from the absorbance at 280 nm and from the molecular extinction coefficient of the antibody at 280 nm. Thus, the labeling number of peroxidase to the antibody can be obtained from the concentrations of peroxide and the antibody.

Thus, the labeling numbers of the labeled anti-chondrocalcin antibodies were determined and the correlation with measurement sensitivity was investigated. As a result, it was evidently shown that one molecule of Fab', F(ab')$_2$ or Facb fragment labeled with 1.0 or more molecules of enzyme is generally used, and the fragments labeled with 1.5 or more enzyme molecules (poly-labeled antibody) give more satisfactory results. In order to obtain sufficient measurement sensitivity to determine chondrocalcin in body liquid, the poly-labeled antibody is preferably composed of one molecule of Fab', F(ab')$_2$ or Facb fragment and more than 1.5 molecule of enzyme, more preferably more than 2 molecules of enzyme. The present invention, however, is not limited thereto.

Such poly-labeled antibody is produced by reaction of the above-mentioned maleimidized antibody or antibody fragment with a thiolated enzyme. As for the reaction conditions, the molar ratio of the fragment of antibody to the said enzyme is 1:1 or more, preferably 1:3 or more; the reaction temperature is 4° to 40° C., preferably 4° to 30° C.; the reaction pH, 5.5 to 7.5; and the reaction time, 5–48 hours. As long as the poly-labeled antibody according to the present invention is obtained, however, the reaction conditions are not limited to those cited above. The poly-labeled antibody obtained by such methods can be isolated and purified from the reaction mixture by gel chromatography.

The enzyme-labeled antibody according to the present invention can exactly determine chondrocalcin in body fluid with sensitivity necessary for determination, as it inhibits nonspecific reactions and inhibitory reactions other than the objective antigen-antibody reaction, occurring when body fluid is used as a specimen.

On the other hand, anti-chondrocalcin antibody immobilized on an insoluble support is obtained as follows.

Insoluble support include naturally occurring polymers their derivatives synthetic polymers and their derivatives. Naturally occurring Polymers and their derivatives include polysaccharides and their derivatives, for example, cellulose, Sephadex, Sepharose, carboxymethylcellulose, nitrocellulose, cellulose acetate, and dextran; and inorganic polymers such as glass or silica gel. Synthetic polymers and their derivatives include vinyl polymers, such as polystyrene, polyethylene, polypropylene, ABS, polyvinyl fluoride, polyamine-methyl vinyl ether-maleic acid copolymer, ethylene-maleic acid copolymer, etc., polycondensation polymers such as polyamides, e.g., nylon 6, nylon 6/6, polyesters, e.g., polyethylene terephthalate, or amino acid polymers. The shape is not particularly limited to test tube, microtiter plate, beads, membrane, etc. The antibodies to be immobilized on the insoluble support are the molecule of anti-chondrocalcin antibody, its fragment maintaining the ability to bond to the antigen, for example, F(ab')$_2$, Fab', Fab, or Facb, or the derivatives of the antibody molecule holding the ability to bond to the antigen and its fragment. These antibodies are immobilized on the insoluble support by physical adsorption, for example, dipping a support such as polystyrene in a solution of anti-chondrocalcin antibody; ionic bonding, for example, using an ion-exchange resin or a support bearing ionizing functional groups, e.g., amino, carboxylic, sulfonic or phosphoric acid group; or covalent bonding by chemical reactions, for example, a carboxyl chloride method, a carbodiimide method, a maleic anhydride derivative method, a cyanogen bromide-activated polysaccharide method, a diazo method, an activated ester method, a support-bonding method using a crosslinking agent (crosslinking agent includes gultaraldehyde, hexamethylene diisocyanate, succinimide or maleimide, and a further the method for bonding through a substance which has no ability to bond to chondrocalcin, but can bond to anti-chondrocalcin antibody by biological reactions, for example, a method using a protein A-bonded support.

The use of an insoluble support whose surface is mirror-finished is preferred, because nonspecific adsorption is reduced, while measurement sensitivity is increased. Mirror-finished insoluble supports include a body having the surface of less than 1.5 $\mu$m centerline average roughness (Ra). The centerline average roughness can be measured by means of a surface roughness-measuring apparatus, for example, Surfcom 570A (Tokyo Precision Co. Ltd.)

Such a mirror-finished insoluble support is not especially limited, as long as the Ra is less than 1.5 μm, but, for example, polystyrene or the like is preferably used.

When the anti-chondrocalcin antibody immobilized on the insoluble support according to the present invention is used, which has been prepared as stated above, a trace amount of chondrocalcin can be determined exactly in body fluid as a specimen.

Subsequently, the method for measuring chondrocalcin according to the present invention will be illustrated, which is characterized by using the reagent prepared by the procedures stated above and mammalian body fluid as a specimen to determine the chondrocalcin in the mammal by utilizing the immune reactions in the solution.

Immunological measurement methods such as the competition method and the sandwich method according to the present invention are used. The sandwich method includes the one-step process and the two-step process.

In the one-step sandwich process, the antigen-antibody reaction between the specimen including the antigen to be determined, the solid-phase antibody immobilized on an insoluble support and an enzyme-labeled antibody is carried out in the same reaction system to form the solid-phase antibody-antigen-labeled antibody complex, followed by washing and determination of the labeled substance. In this case, the reaction may be conducted either in the coexistence of the specimen. the solid-phase antibody and the labeled antibody or sequentially the reaction between the specimen and the solid-phase antibody may be followed by addition of the labeled antibody for reaction, or the reaction of the specimen with the labeled antibody may be followed by addition of the solid-phase antibody. Any procedures can be adopted, as long as the solid-phase antibody-antigen-labeled antibody complex is formed before washing.

On the other hand, in the two-step sandwich method, the reaction of the specimen with the solid-phase antibody is first conducted to form the solid-phase antibody-antigen complex, then the remaining specimen is removed and washed off, and the labeled substance is added to form the solid-phase antibody-antigen-labeled antibody complex. After washing, the labeled substance is determined.

In the present invention, the two-step process can be suitably applied to cases where the specimen of body fluid contains substances which disturb the measurement or those which cause nonspecific reactions. In this process, after reaction of the antigen in the specimen with the solid-phase antibody, the specimen is removed and washed, and the labeled antibody is allowed to act, thus the reaction of the labeled antibody is not influenced by the above-stated substances with the accuracy and sensitivity increased. In the meantime, the two-step process has problems of more complicated operations in comparison with the one-step process, for example, the increased times of washing operations and the prolonged operation time. The one-step sandwich process also can be adopted. This process is one of preferred embodiments, because it is simple in operation and has a short reaction time, but it is generally susceptible to body fluid. In other words, the sensitivity of the process is lowered or becomes insufficient by nonspecific reactions and inhibition of the immune reactions.

In the present invention, for example, when a mirror-finished, insoluble support, especially beads having a surface of less than 1.5 μm centerline average roughness, are used as an insoluble support, and a multi-labeled $F(ab')_2$ is employed as a labeled antibody, nonspecific adsorption to said beads is inhibited and the sensitivity is increased by the multi-labeled antibody $F(ab')_2$, whereby the one-step sandwich process becomes adequately possible.

In the determination method according to the present invention, it is preferred that a protein of 16,000 to 50,000 molecular weight and 1.0 to 5.0 isoelectric point or a mixture thereof is added to the immune reaction solution, until the final concentration reaches 0.02 to 0.9% by weight in the immune reaction solution, because the nonspecific adsorption is inhibited, and, consequently the back ground is remarkably lowered and the sensitivity is increased. Such protein or a mixture thereof can be added to the immunoassay reagent according to the present invention until the concentration of the protein reaches a prescribed value.

The protein is, for example, casein, pepsin, ovoglycoprotein, orosomucoid or the like. Such mixture can contain 10 to 60% by weight, preferably 20 to 50% by weight of the above-stated protein, 30 to 80% by weight, preferably 40–60% by weight of saccharide, e.g., lactose, other lipids (for example, 0.5–2% by weight), ash (for example, 5–12% by weight) and water (for example, 2 to 8% by weight).

One of the typical mixtures is skim milk. Skim milk contains casein as a protein and characteristically shows a better dispersion ability in the immune reaction solution, higher NBS (nonspecific binding) effect per gram of protein and better storability (resistant to form precipitation) at 4° C., than in the case of casein only. In the present invention, any defatted milk can be used as a skim milk according to the present invention, regardless of its origination. One of the most typical one is the commercially available skim milk produced by Difco Company.

In the present invention, the molecular weight of protein means the value measured according to the osmotic pressure method. In more detail, the molecular weight is measured by utilizing the fact that the difference in osmotic pressure can be a parameter for the molecular weight of the protein, where the pressure difference between the high polymer solution and the pure solvent both of which are separated with a semipermeable membrane which can pass through the solvent, but not the high polymer.

In present invention, 6.66M urea solution is used and the osmotic pressure was measured at 4° C. The isoelectric point means the value measured according to the chromatographic focussing method where the protein is separated at the isoelectric point. In more detail, a column (measuring 0.5 cm diameter × 45 cm length) is filled with PBE94 gel (Pharmacia Co. Ltd.) and 0.025M imidazole hydrochloride buffer solution (pH 7.4) is used for elution.

Any kinds of usual solvents can be used as a solvent for the immune reaction, as long as they do not cause adverse effect on the reaction. For example, phosphate buffer solution, tris hydrochloride buffer solution, acetate buffer solution at 6.0 to 8.0 pH are preferred.

The temperature of the immune reaction at the measurement is not especially limited, as long as the constituent protein is not denatured, and the immune reaction is not markedly inhibited. However, in general, the reaction is satisfactorily conducted lower than 50° C., preferably at about 4° C. to about 45° C. for about 5 minutes to about 20 hours.

The mammalian body fluid for measurement according to the present invention means the body fluid of a mammal such as human or equine containing factors inhibiting the specific reactions and causing nonspecific reactions and may be in the form of usual clinical samples, for example, blood in the form of serum or plasma, joint fluid, lymph, thymic fluid, ascitic fluid, amniotic fluid, cell tissue fluid, myeloid fluid or urine.

In the present invention, the anti-chondrocalcin antibody immobilized on the insoluble support and labeled anti-chondrocalcin antibody can be combined with other substances necessary for the immunoassay to give a kit for determining chondrocalcin. The other substances for immunoassay are, for example, a solubilizer, a washing agent, a substrate for measuring the enzyme activity and a reaction terminator, which are known.

Thus, according to the present invention, a sample containing a trace amount of mammalian chondrocalcin such as a clinical sample, is used as a specimen, to determine the chondrocalcin in the sample in high sensitivity and accuracy through simple operations.

The possibility of industrial application:

The values of chondrocalcin in body fluid which are determined using the immunoassay and the reagent according to the present invention are useful in diagnosis and monitoring the treatment of cartilage diseases of mammalian animals, for example, horse arthropathy or human chondrocyte-related diseases. Especially, it can be used for diagnosis and treatment monitoring of human osteoarthritis and discriminative diagnosis between osteoarthritis and rheumatoid arthritis.

The present invention will be illustrated in detail by the examples and comparisons. In the examples, % means percent by weight.

EXAMPLE 1

(1) Preparation of bovine chondrocalcin

According to the method by H. U. Choi, 10.0 mg of bovine chondrocalcin were obtained from the cartilage of 20 long tubular bones of bovine fetal limbs. The SDS-PAGE electrophoresis gave a single band of 35,000 molecular weight.

(2) Preparation of antigen-stimulating lymphocytes

An emulsion of 90 μg of bovine chondrocalcin and Freund's complete adjuvant was given intraperitoneally to male B alb/c mouse. After that, an emulsion of 40 to 50 μg of bovine chondrocalcin and Freund's incomplete adjuvant were given 5 times at 3 to 4-week intervals. On the tenth day after the 5th administration, 60 μg of chondrocatcin were dissolved in 1.0 ml of physiological saline solution and given intravenously. The spleen was enucleated aseptically 4 days later, passed through a mesh made of stainless steel to give a spleen cell suspension in the RPMI-1640 medium supplemented with 0.39 g/l of L-glutamine, 0.2 g/l of Kanamycin sulfate and 2.0 g/l of sodium hydrogen carbonate. Said suspending cells were washed 3 times with the medium to give the spleen cell suspension.

(3) Cell fusion

Mouse myeloma cells P3U1 were cultured in the GIT synthetic medium (DAIGO EIYO Chemical Co. Ltd.) supplemented with 0.2 g/l of Kanamycin sulfate. The myeloma cells were on the logarithmic phase. The spleen cells and the myeloma cells were suspended in a serum-free RPMI-1640 medium at a cell number ratio of 3:1 and centrifuged at 1,300 rpm for 5 minutes. After removal of the medium, the cell precipitate was suspended, as 50% solution of polyethylene glycol of 1,500 average molecular weight (7.2 pH) was quietly added by 1 ml. The suspension was combined with 9 ml of the serum-free RPMI-1640 medium, and the cells were carefully stirred. The mixture was centrifuged at 1,000 rpm for 5 minutes, the supernatant was removed, the cell precipitate was collected and suspended in 40 ml of HAT medium.

(4) Cloned hybridoma

The fused cell suspension was distributed on the 96 microplate (200 μl every well). The plate was cultured at 37° C. in 5% CO atmosphere. The half amount of the medium was exchanged with the virgin HAT medium 1 day and two days later, and the operation was repeated at 2-day interval. After 11 days, the antibody against bovine chondrocalcin in the supernatant of hybridoma culture mixture was screened by the enzyme immunoassay. The antigen used in the screening was bovine chondrocalcin and the second antibody was alkali-phosphatase-labeled goat anti-mouse IgG antibody.

Among 192 wells to which the hybridoma was distributed, the colonies of the fused cells were observed in 102 wells and the 7 wells in the 102 wells were antibody-positive. The hybridomas in the antibody-positive wells were diluted so that every well of the 96 microplate includes 0.9 cell. Then, Balb/c mouse thymus cells were distributed to the microplates as feeder cells and they were cultured in the GIT culture medium supplemented with 0.2 g/l of kanamycin sulfate. The single colony was confirmed by microscopic observation. The antibody against bovine chondrocalcin in the supernatant of the hydridoma culture was screened by the enzyme immunoassay. Each well was found to be antibody-positive and produce anti-bovine chondrocalcin monoclonal antibody.

(5) Culture of hybridoma

These cloned hybridomas were injected into the abdominal cavities $10^6$–$10^7$ cells/every Balb/c mouse to which 0.1 ml of pristane (WAKO Pure Chemical Co. Ltd.) had been given intraperitoneally 2 weeks ago. Then, ascites was collected 2 to 3 ml/mouse on the 7th to 10th day.

(6) Purification of monoclonal antibody The collected ascites was purified according to the method by Ey et al [see P. L. Ey et al., *Immunochemistry*, 15, 429–436 (1978)]. In other words, 2 to 3 ml of the ascites fluid was fed to a protein A-Sepharose column (gel volume: 5 ml) equilibrated with 0.1M phosphate buffer solution (pH 8.0) and the monoclonal antibody was eluted using, in turn, 0.1M sodium citrate buffer solutions of 6.0, 5.0, 4.0 and 3.0 pH to collect the purified monoclonal antibody, namely Chon-3F, Chon-5G, Chon-8G and Chon-4H.

(7) Class of purified monoclonal antibodies

The specific class of the purified monoclonal antibodies was determined by the Ouchterlony gel diffusion test using the class-specific anti-mouse antiserum. The results are given in Table 1.

TABLE 1

| Antidody | $IgG_1$ | $IgG_{2a}$ | $TgG_{2b}$ | $IgG_3$ | IgM |
|---|---|---|---|---|---|
| Chon.-3F | − | + | − | − | − |
| Chon.-5G | − | − | + | − | − |
| Chon.-8G | − | + | − | − | − |
| Chon.-4H | − | + | − | − | − |

(8) Search on whether the recognition sites by the monoclonal antibodies are identical or different The bovine chondrocalcin PBS solution of 2 μg/ml was distributed to 96 microplate 150 82 g/l every well, allowed to stand one overnight at 4° C., washed with PBS, combined with 0.5% BSA-PBS, and left to stand further one overnight, whereby an antigen-immobilized plate was prepared. This plate was combined with 150 μl/ml monoclonal antibody PBS solution (the first antibody) in each well and they were allowed to stand for 75 minutes at 37° C. After the wells were washed, 0.5% solution of the monoclonal antibody labeled with horse raddish peroxidase (the second antibody) in BSA-PBS was added to the wells 150 μl every well and they were allowed to react at 37° C. for 60 minutes. After rinsing with physiological saline solution, the HRP substrate solution (containing 50 mg/dl of 2,2'-azino-di[3-ethyl-benzthiazolinesulfonate (6)]diammonium salt and 50 μl/dl of 2M hydrogen peroxide in 0.1M phosphate/citrate buffer solution (pH 4.5) was added by 150 μl to emit fluorescence at 25° C. for 6 minutes. The reactions were terminated with 50 μl of 0.1M aqueous oxalic acid and the measurement was carried out using a plate reader at 415 nm wavelength.

It is obvious from the results shown in Table 2, that the four monoclonal antibodies are three kinds of antibodies having different epitopes, and Chon-5G and Chon-4H have the same or close epitope and cannot bind simultaneously.

TABLE 2

| First antibody | Second antibody | Absorbance |
| --- | --- | --- |
| Chon.-3F | Chon.-4H | 0.450 |
| Chon.-5G | | 0.198 |
| Chon.-8G | | 0.503 |
| Chon.-4H | | 0.185 |
| Chon.-3F | Chon.-5G | 0.195 |
| Chon.-5G | | 0.002 |
| Chon.-8G | | 0.189 |
| Chon.-4H | | 0.001 |

EXAMPLE 2

An emulsion of 1 mg of bovine chondrocalcin purified in Example 1 and Freund's complete adjuvant was subcutaneously given to rabbits. After 19 days, 450 μg of bovine chondrocalcin was subcutaneously administered in the same manner. After additional 16 days, an emulsion of 450 μg of bovine chondrocalcin and Freund's complete adjuvant was subcutaneously given. On the 10th day after the final administration, the blood was collected, prepared into serum and subjected to enzyme immunoassay. In other words, bovine chondrocalcin was used as an antigen, and horse radish peroxidase-labeled goat anti-rabbit IgG antibody, as the second antibody, to measure the antibody value against bovine chondrocaicin and it was found to 400,000 folds. Then, the whole blood was collected to prepare serum and the serum was precipitated with 40% saturated ammonium sulfate solution, and purified with protein A-Sepharose-4B column to obtain the polyclonal antibody against bovine chondrocalcin.

EXAMPLE 3

Chon.-5G, the monoclonal antibody described in Example 1 was dissolved in 0.1M phosphate/citrate buffer solution (pH 4.0) in 20 μg/ml concentration, and the solution was distributed to a microplate 100 μl every well and immobilized by allowing it to stand at 4° C. for 24 hours. The product was washed with PBS, combined with 0.5% BSA-PBS 100 μl every well, allowed to stand one overnight at 4° C. to effect after-coating, finally washed with PBS whereby an Chon.-5G-immobilized plate was obtained.

Subsequently, a dilution series of the purified bovine chondrocalcin, 15, 10, 5, 1.5 and 0 ng/ml was prepared using PBS, added to the Chon.-5G-immobilized plate 100 μl every well, and allowed to react at 37° C. for 1 hour. After washing with PBS, 100 μl of HRP substrate (TMB) was added to develop the color at 37° C. for 30 minutes, then the reaction was stopped by adding 100 μl of 1N sulfuric acid solution, and the absorbance was measured with a plate reader at 450 nm wavelength.

The resulting calibration curve is given in FIG. 1.

EXAMPLE 4

Chon.-3F, the monoclonal antibody described in Example 1, was dissolved in 0.1M phosphate/citrate buffer solution so that the protein concentration became 20 μg/ml, then polystyrene beads were dipped in the solution 3 days and nights whereby the antibody was immobilized to the beads. After being washed with PBS, the beads were dipped in BSA-PBS one overnight to effect after-coating, rinsed with PBS again to give Chon.-3F-immobilized beads.

A dilution series of the purified bovine chondrocalcin, 15, 10, 5, 1.67 and 0 ng/ml, was prepared using PBS and these solutions were allowed to react with the Chon.-3F-immobilized beads at 37° C. for 1 hour. After being rinsed with PBS, 0.5% solution of horse radish peroxidase (HRP)-labeled polyclonal antibody (described in Example 2) in BSA-PBS was added to the beads in an amount of 400 μl and they were allowed to react at 37° C. for 1 hour. After being washed with PBS, 400 μl of HRP substrate (containing 0.125% of 3,3',5,5'-tetramethylbenzidine and 0.03 5 of hydrogen peroxide in 0.1M phosphate/citrate buffer solution (pH 4.5) was added to emit the light at 37° C. for 30 minutes. The reaction was terminated with 1.0 ml of 1N-sulfuric acid and the absorbance was measured with a spectrophotometer at 450 nm wavelength.

Figure 2:
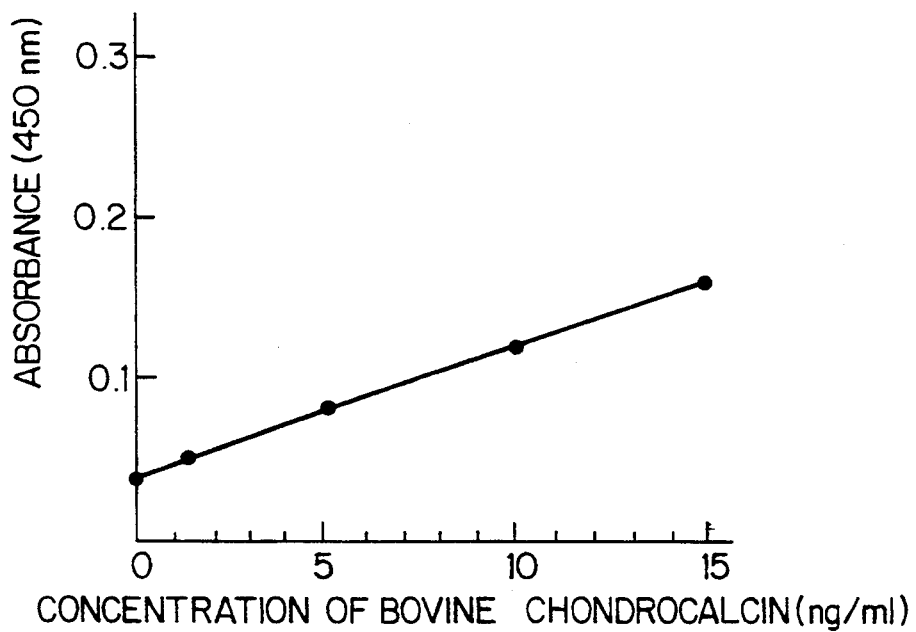
FIG. 2 is a calibration curve for bovine chondrocalcin using a monoclonal antibody "Chon-3F" and a polyclonal antibody labeled with HRP as reagents for determination.

The resultant calibration curve is given in FIG. 2.

EXAMPLE 5

According to the process described in Example 4, beads to which the polyclonal antibody against bovine chondrocalcin (described in Example 2) was immobilized were prepared.

Figure 3:
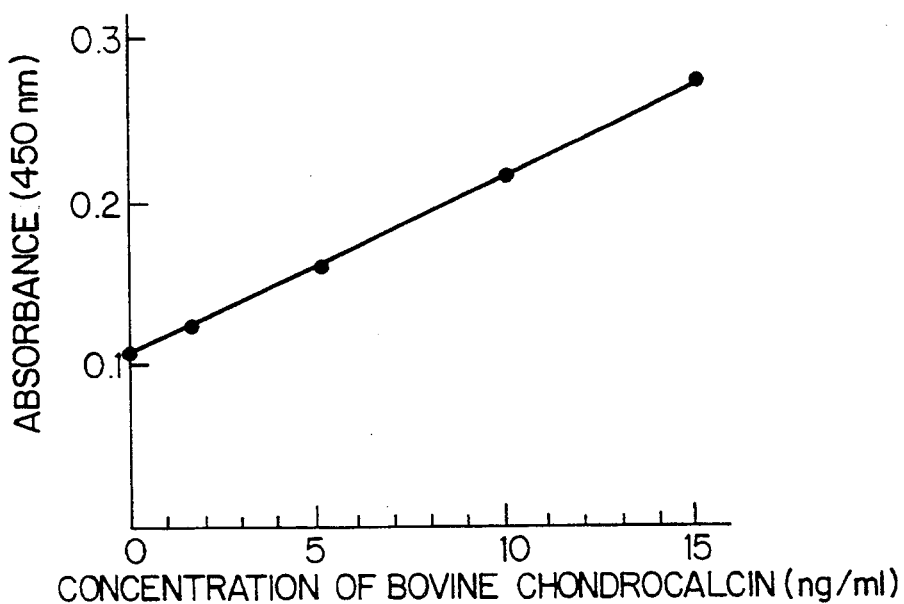
FIG. 3 is a calibration curve for bovine chondrocalcin using a polyclonal antibody and a monoclonal antibody labeled with HRP "Chon-4H" as reagents for determination.

Then, a dilution series of purified bovine chondrocalcin 15, 10, 5, 1.67 and 0 ng/ml was prepared using PBS and 400 μl each was added to a glass tube and allowed to react with the immobilized beads at 37° C. for 1 hour. After rinsing with PBS, 400 μl of 0.5% Chon.-4H (described in Example 1), HRP-labeled monoclonal antibody solution in BSA-PBS was allowed to react at 37° C. for 1 hour. As in Example 4, the calibration curve of FIG. 3 was obtained.

EXAMPLE 6

A dilution series of purified bovine chondrocalcin, 10.0, 5.0, 1.0, 0.6, 0.4, 0.2 0.1 and 0.0 ng/ml was prepared using PBS. Each bovine chondrocalcin was combined with normal human plasma which had been passed through a column filled with Sepharose-4B to which the polyclonal antibody against bovine chondrocalcin (described in Example 2) was immobilized, in an equal volume to prepare a series of dilution system containing chondrocalcin 5.0, 2.5, 0.5, 0.3, 0.2, 0.1, 0.05, 0.0 ng/ml in two-fold diluted human plasma, respectively.

Figure 4:
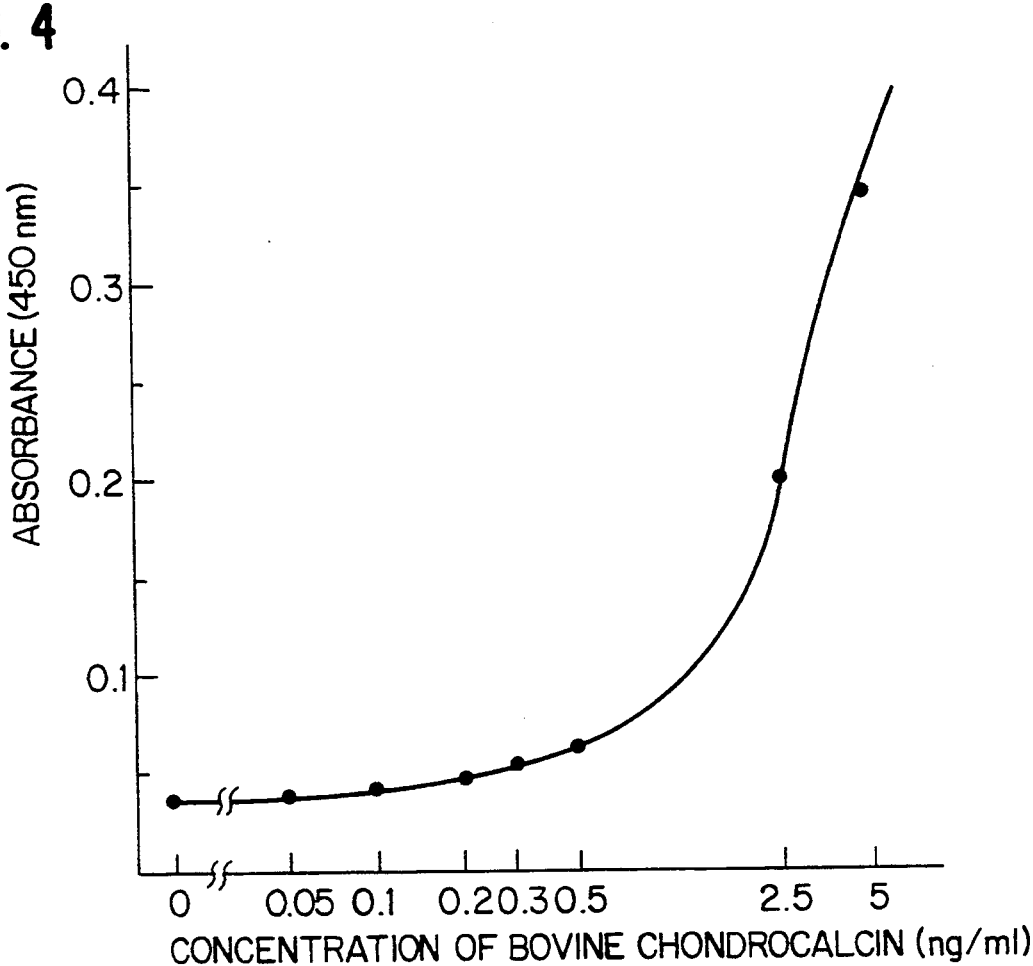
FIG. 4 is a calibration curve for determination of human chondrocalcin in a specimen.

The dilution series of bovine chondrocalcin solutions was measured using Chon.-4H (described in Example 1)-immobilized plate which had been prepared as in Example 3 and the HRP-labeled polyclonal antibody (described in Example 2) to make a calibration curve of FIG. 4.

Subsequently, serum or synovial fluid was combined with an equal volume of PBS, respectively and the absorbance of the 2-fold diluted samples was measured as in Example 3, and the concentration of human chondrocalcin converted into ovine chondrocalcin was calculated from the calibration curve in FIG. 4. The results are summarized in Table 3.

TABLE 3

| No. | Diseases | Fluid | Absorbance | Concentration |
|---|---|---|---|---|
| 1 | Normal | serum | 0.028 | 0.0 (ng/ml) |
| 2 | osteosarcoma | serum | 0.062 | 1.1 |
| 3 | osteoarthritis | synovial fluid | 0.093 | 2.0 |
| 4 | osteoarthritis | synovial fluid | 0.333 | 9.0 |

EXAMPLE 7

The anti-bovine chondrocalcin polyclonal antibody described in Example 2 was dissolved in 0.1M phosphate/citrate buffer solution (pH 4.0) to form 20 μg/ml solution and the solution was distributed on a microplate 100 μl every well and immobilized by leaving it to stand at 4° C. for 24 hours. The products were washed with PBS, after-coated by adding 0.5% BSA-PBS 100 μl every well and allowing them to stand one overnight at 4° C., and rinsed with PBS, to give bovine chondrocalcin polyclonal antibody-immobilized plates.

Then, a dilution series of purified bovine chondrocalcin, 15, 10, 5, 1.5, 0 ng/ml was prepared using 1% BSA-final concentration 0,065% skim milk-PBS solution and distributed. to the antibody-immobilized plate 100 μl every well so that they were allowed to react at 37° C. for 1 hour. They were washed with PBS, 0.5% solution of HRP-labeled anti-bovine chondrocalcin polyclonal antibody in 0.5% BSA-0.1% skim milk-PBS solution was distributed 100 μl every well to effect the reaction at 37° C. for 1 hour. After PBS washing, the substrate for HRP (containing 2.5 mM hydrogen peroxide and 0.0225% 3.3′, 5,5′-tetramethylbenzidine) was added to individual wells 100 μl every well to develop the color at 37° C. for 30 minutes. Then, 100 μl of 1N-sulfuric acid was added to terminate the reaction, then the absorbance was measured with a plate reader at 450 nm wavelength.

Figure 5:
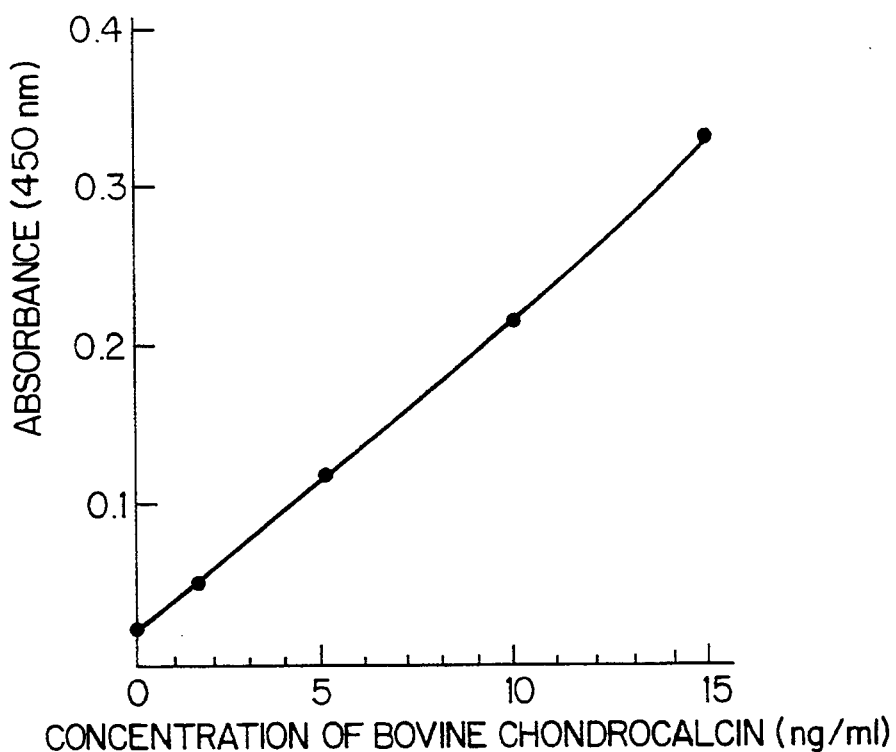
FIG. 5 is a calibration curve for bovine chondrocalcin using reagents according to the present invention: anti-chondrocalcin polyclonal antibody and anti-chondrocalcin polyclonal antibody labeled with HRP.

The resultant calibration curve is shown in Fig. 5.

The lower limit of the measurement was 1 ng/ml and it was markedly higher sensitivity than that of the radioimmunoassay according to A. Hinek et al., 100 ng/ml [see *J. Cell Biol.*, 104, 1435–1441 (1987)].

EXAMPLE 8

Figure 6:
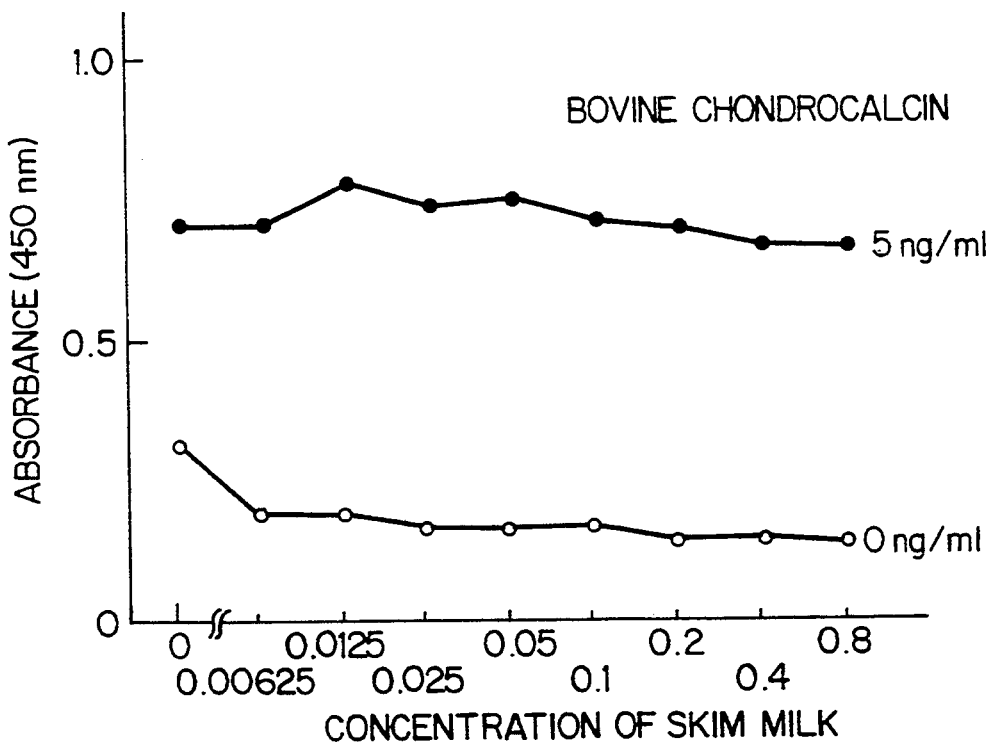
FIG. 6 shows the effect of skim milk added to the chondrocalcin determination system.

Bovine chondrocalcin was diluted with the buffer solution for the immunoassay (1% BSA-containing 0.01M phosphate and 0.85% NaCl buffer solution (pH=7.2), abbreviated to 1% BSA-PBS hereinafter) to prepare 0 and 10 ng/ml solutions. The solution, 50 μl was thoroughly mixed with 50 μl of skim milk solutions of 0, 0.00625, 0.0125, 0,025, 0.05, 0.1, 0.2, 0.4 and 0.8% final concentrations in the same buffer solution, then the solution was distributed to the microplate to which the anti-bovine chondrocalcin polyclonal antibody described in Example 2 had been immobilized 100 μl every well to conduct the reaction at 37° C. for 2 hours (the first reaction). Then, the reaction mixture was washed with PBS-0.05% Tween-20, the HRP-labeled anti-bovine chondrocalcin antibody which had been prepared as described in Example 3, is diluted with a buffer solution for immunoassay containing skim milk whose final concentration becomes the same as in the first reaction, and the resultant solution was added to each well by 100 μl to conduct the reaction at 37° C. for 1 hour (the second reaction). After rinsing with PBS-0.05% Tween-20, the substrate for HRP described in Example 3 was added by 100 μl to develop the color at 37° C. for 30 minutes, then 1N sulfuric acid was added by 25 μl to terminate the reaction. The absorbance was measured with a plate reader at 450 nm wavelength. The results are given in FIG. 6. As shown evidently from the figure, skim milk can inhibits the nonspecific adsorption at a concentration higher than 0.00625%.

EXAMPLE 9

The Fab′ fragment of anti-bovine chondrocalcin polyclonal antibody (Anti-chondrocalcin PCA) described in Example 2 was allowed to bond to peroxidase according the process based on the Nisonoff's method to prepare a peroxide-labeled Fab′ (see the lecture course of experimental biochemistry, the second series, Vol. 5 page 109 to 112, edited by the Biochemical Society of Japan, published by Tokyo Kagaku Dojin Co. Ltd. (Japan) (1986). In other words, 1250 μg of anti-chondrocalcin PCA was dissolved in 1.25 ml of 0.2M sodium acetate buffer solution (pH 4.5) and dialyzed against the buffer solution. Pepsin 25 μg was added to digest the dialyzate at 37° C. for 24 hours. Sodium hydroxide 1N solution was added dropwise to the reaction mixture until the pH rose up to 8 to terminate the reaction. The F(ab′)$_2$ fragment of 92,000 molecular weight was separated from the reaction mixture through TSK gel 3000SW column-HPLC using 5 mM EDTA-0.1M sodium phosphate buffer solution (pH 6.0) as an eluent. The product was concentrated by ultrafiltration to collect 2.2 ml of F(ab′)$_2$ solution in 122.3 μg/ml concentration. The product was combined with 245 μl of 0.1M 2-mercaptoethylamine to effect reductive treatment at 37° C. The reaction mixture was concentrated by ultrafiltration and the Fab′ fragment of 46,000 molecular weight was separated through HPLC as in F(ab′)$_2$. 2.0 ml of Fab′ fragment solution of 83.7 μg/ml concentration was obtained.

In the meantime, 4.0 mg of horse radish peroxidase (Toyo Spinning Co. Ltd.; abbreviated to HRP) was dissolved in 0.6 ml of 0.1M sodium phosphate buffer solution (pH 7.0), 40 μl of N-succinimidyl-3-maleimide benzoate solution in dimethylformamide (31.4 mg/ml concentration) was added dropwise thereto to conduct the reaction at 30° C. for 1 hour. The reaction mixture was fed into a Sephacryl S-200 column and eluted with 0.1M sodium phosphate buffer solution (pH 6.0) to separate maleimide-HRP.

Then, 470 μl of 3.10 mg/ml maleimide-HRP was added dropwise to the above-stated Fab′ fragment solution to conduct the reaction at 4° C. for 20 hours. The reaction mixture was concentrated by ultrafiltration, and HRP-labeled Fab′ of 86,000 molecular weight was obtained by the TSK gel 3,000 SW column-HPLC eluted with PBS (pH 7.2). The labeled Fab' was used to make the following calibration curves.

The anti-chondrocalcin PCA described in Example 2 was dissolved in 0.1M phosphate/citrate buffer solution (pH 3.5) to prepare a solution of 20 μg/ml concentration. The solution was distributed to a microplate 100 μl every well and immobilized by allowing to stand at 4° C. for 24 hours. After being rinsed with PBS, 1.0% BSA-PBS was added 100 μl every well and left to stand at 4° C. for 24 hours to form the after coat, then rinsed with PBS to give anti-chondrocalcin PCA-immobilized plates.

A dilution series of purified bovine chondrocalcin, 0, 10, 50, 100, 500, 1,000, 5,000, 10,000 pg/ml was prepared using 1% BSA-final concentration 0.1% skim milk-PBS (pH 7.2) and they were added to the antibody-immobilized plate 100 μl every well to carry out the reaction at 37° C. for 5 hours, and additionally at 4° C. for 24 hours. The reaction mixture was washed with PBS-0.05% Tween-20, then diluted with 1.0% BSA-final concentration 0.1% skim milk-PBS (pH 7.2) so that the concentration of the Fab' component in the HRP-labeled anti-chondrocalcin PCA Fab' became 60 ng/ml. The prepared labeled Fab' solution was distributed 100 μl every well to conduct the reaction at 20° C. for 4 hours. The reaction mixture was rinsed with PBS-0.05% Tween-20, then a substrate for HRP (containing 2.5 mM of hydrogen peroxide and 0.0225% of 3,3', 5,5'-tetramethylbenzidine) to develop the color at 20° C. for 2 hours. Then, 25 μl of 1N-sulfuric acid solution was added to terminate the reaction and the absorbance was measured with a plate reader at 450 nm wavelength.

Figure 7:
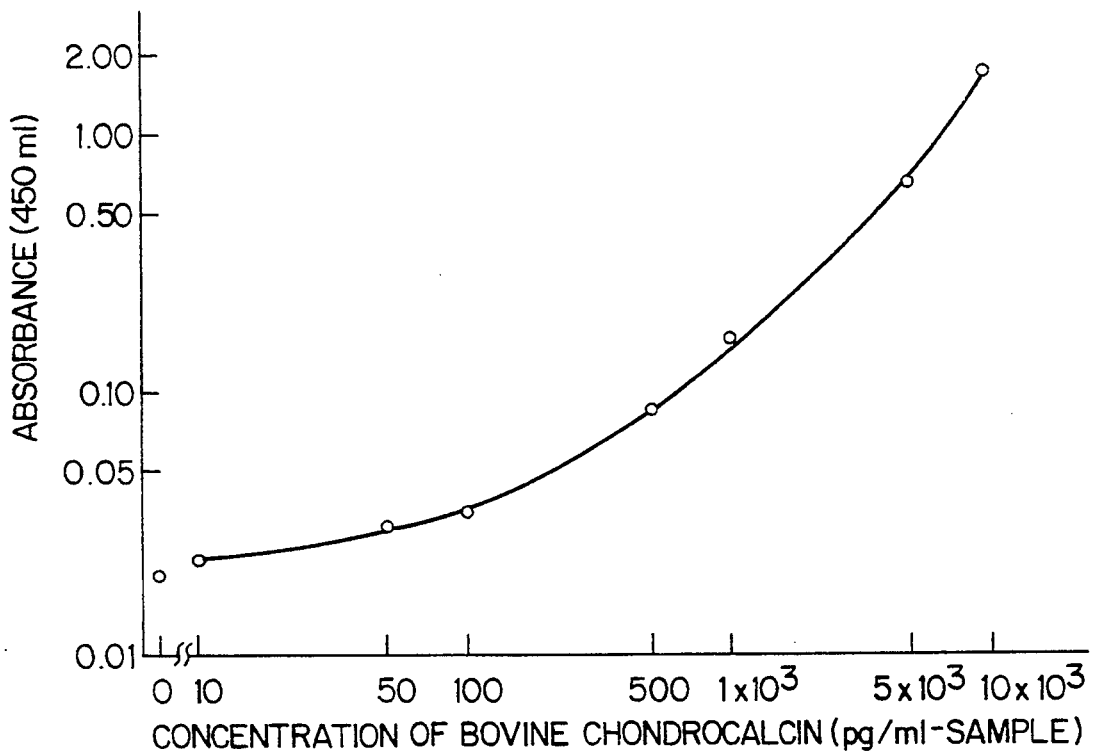
FIG. 7 is a calibration curve for bovine chondrocalcin using anti-chodrocalcin polyclonal antibody and anti-bovine-chondrocalcin polyclonal antibody, Fab', labeled with peroxidase as reagents.

The calibration curve in FIG. 7 was obtained from the results.

As evidently shown in FIG. 7, the lower limit of the measurement was 10 pg/ml and considerably higher sensitive than that of the radioimmunoassay, 100 ng/ml according to Hinek et al [see *J. Cell. Biol.* 104, 1435–1441 (1981)].

EXAMPLE 10

The Fab' fragment of Chon.-4H, anti-bovine chondrocatcin MCA, described in Example 1, was prepared according to the Parham's method [see the lecture course of experimental biochemistry, the second series, Vol. 5 page 100, edited by the Biochemical Society of Japan, published by Tokyo Kagaku Dojin Co. Ltd. (Japan) (1986)] and HRP-labeled Fab' was obtained in the same way as in Example 8. In other words, 480 μg of Chon.-4H was dissolved in 0.1M sodium citrate buffer solution (pH 4.1) to prepare a solution of 2.0 ml. Then, the solution was dialyzed against the same buffer solution. The product was digested with 56.25 μg of pepsin at 37° C. for 90 minutes. To the reaction mixture, 1N NaOH was added dropwise until the pH rose up to 8 to terminate the reaction. The reaction mixture was subjected to TSK gel 3,000 SW column-HPLC using 5 mM EDTA-0.1M sodium phosphate buffer solution (pH 6.0) to separate F(ab')$_2$ fragment of 92,000 molecular weight. The product was concentrated to give 7.5 ml of F(ab')$_2$ solution of 19.6 μg/ml concentration. Then, 835 μl of 0.1M 2-mercaptoethanolamine was added to effect reductive treatment at 37° C. for 2 hours. From this reaction mixture, 5.5 ml of Fab' fragment solution of 9.5 μg/ml concentration was obtained as in Example 9.

Subsequently, 146 μl of 3.10 mg/ml of maleimide-HRP was added dropwise to the Fab' fragment solution to conduct the reaction at 4° C. for 20 hours. HRP-labeled Fab' was obtained form the reaction mixture in the same way as in Example 8. The labeled Fab' was used to provide the following calibration curve.

The immobilized plate used here was prepared in Example 9.

A dilution series of purified bovine chondrocalcin, 0, 10, 50, 100, 500, 1,000 5,000 and 10,000 pg/ml was prepared using 1% BSA 0.1% skim milk-PBS (pH 7.2) and distributed to the antibody-immobilized plate 100 μl every well to conduct the reaction at 37° C. for 2 hours. After being washed with PBS-0.05% Tween 20, the HRP-labeled Fab' obtained from Chon.-4H was diluted with 1% BSA-final concentration 0.1% skim milk-PBS (pH 7.2) so that the concentration of the Fab' component became 300 ng/ml, and the prepared labeled Fab' solution was distributed 100 μl every well to effect the reaction at 37° C. for 1 hour. After rinsing with PBS-0.05% Tween 20, the substrate for HRP (containing 2.5 mM hydrogen peroxide and 0.0255% of 3,3', 5,5'-tetramethylbenzidine) was added 100 μl every well to develop the color at 20° C. for 30 minutes, then 25 μl of 1N sulfuric acid was added to terminate the reaction, and the absorbance was measured with the plate reader at 450 nm wavelength.

Figure 8:
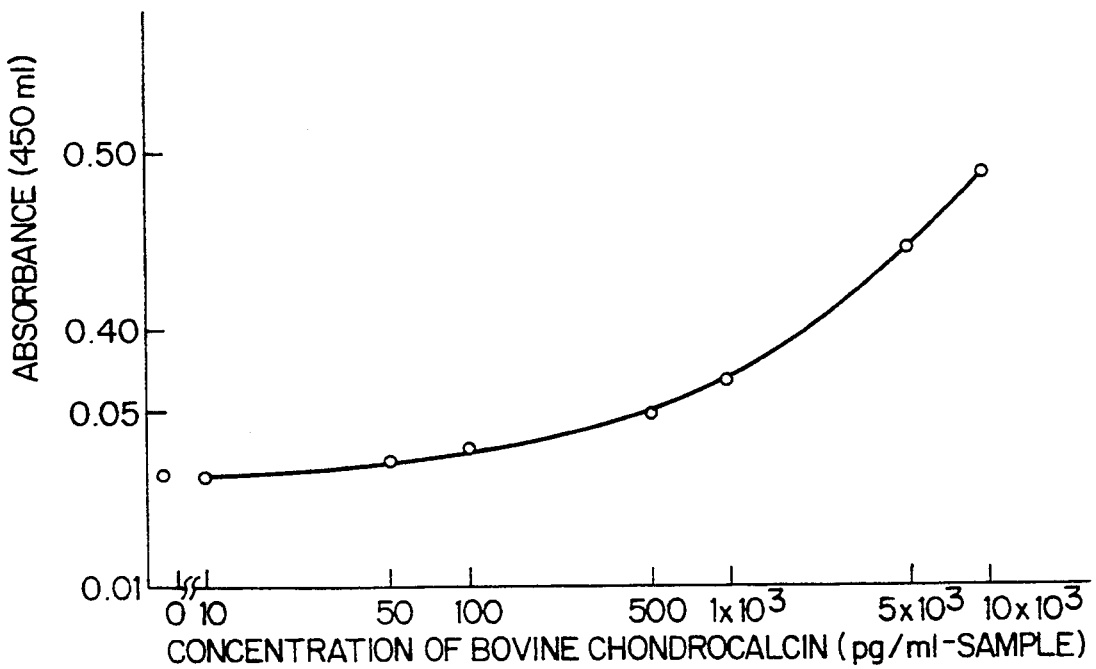
FIG. 8 is a calibration curve for bovine chondrocalcin using anti-chondrocalcin polyclonal antibody and Fab' of anti-bovine-chondrocalcin monoclonal antibody, "Chon-4H", labeled with peroxidase.

FIG. 8 shows the calibration curve obtained from the result. The lower limit of the measurement was 50 pg/ml, and the sensitivity was considerably higher than that in the method according to A. Hinek, et al., 100 ng/ml.

EXAMPLE 11

Figure 9:
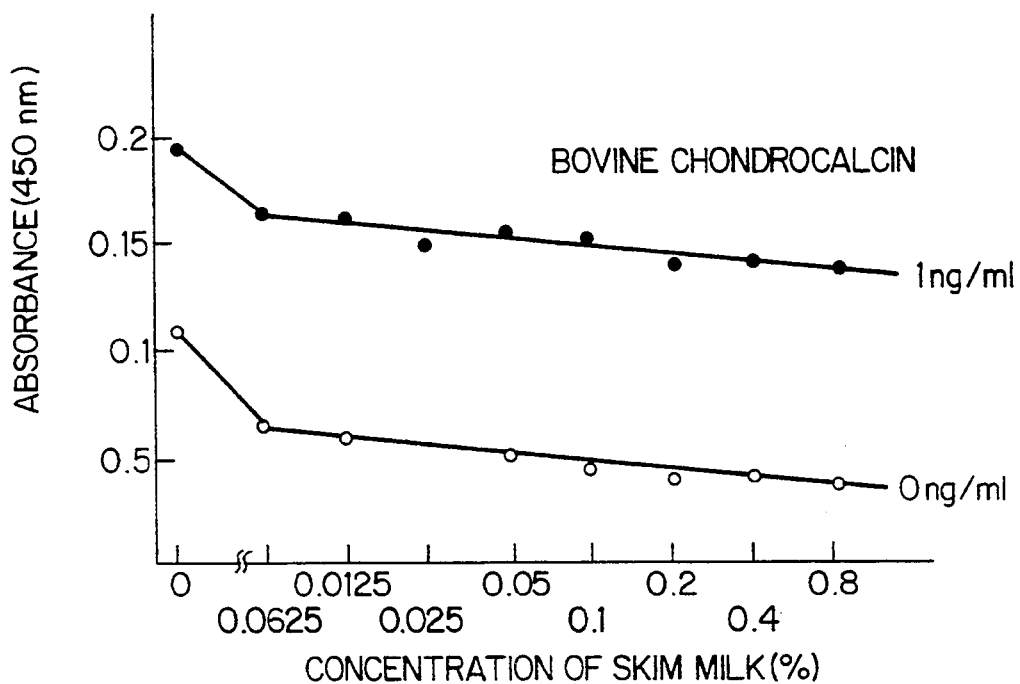
FIG. 9 shows the effect of skim milk added to the chondrocalcin determination system using Fab'. In the Figure, the black dots and white dots give final bovine chondrocalcin concentration 1 ng/ml and 0 ng/ml, respectively.

Bovine chondrocalcin was diluted with the buffer solution for immunoassay (1% BSA-containing 0.01M phosphate 0.85% NaCl buffer solution (pH 7.2), abbreviated to 1% BSA-PBS hereinafter) to prepare 0.2 ng/ml solution. Then, 50 ml of the solution was thoroughly mixed with 50 μg of solutions containing skim milk in the final concentrations of 0, 0.00625,, 0.0125, 0,025, 0.05, 0.1, 0.2, 0.4 and 0.8%. Then, 100 ml of the solution was distributed to the anti-chondrocalcin PCA-immobilized plate prepared as in Example 8 to effect the reaction at 37° C. for 2 hours (the first reaction). After rinsing with PBS-0.05% Tween-20, the HRP-labeled Fab' prepared as in Example 8 was diluted with a buffer solution for immunoassay containing skim milk so that the final concentration became equal to that in the first reaction, then distributed 100 ml every well to effect the reaction at 37° C. for 1 hour (the second reaction). After rinsing with PBS-0.05% Tween-20, the substrate for HRP described in Example 8 was added by 100 μl to develop the color at 37° C. for 0.5 hour, and 25 μl of 1N sulfuric acid was added to terminate the reaction. The absorbance was measured with a plate reader at 450 nm wavelength. The results are given in FIG. 9. As shown evidently in the figure., nonspecific adsorption can be inhibited with skim milk in the concentration higher than 0.00625%.

EXAMPLE 12

A dilution series of purified bovine chondrocalcin, 0, 7.5, 37.5, 75, 375, 750, 3,750, and 7,500 pg/ml was prepared using 1% BSA-final concentration 0.00625% skim milk-PBS (pH 7.2). The each solution was combined with ¼ volume of normal human plasma which had been passed through a column filled with anti-chondrocalcin PCA-immobilized Sepharose 4B to prepare a dilution series of bovine chondrocalcin containing 5-fold diluted human plasma. In the dilution series, bovine chondrocalcin is included in plasma, 0, 30, 150, 300, 1,500, 3,000, 15,000, and 30,000 pg/ml.

Figure 10:
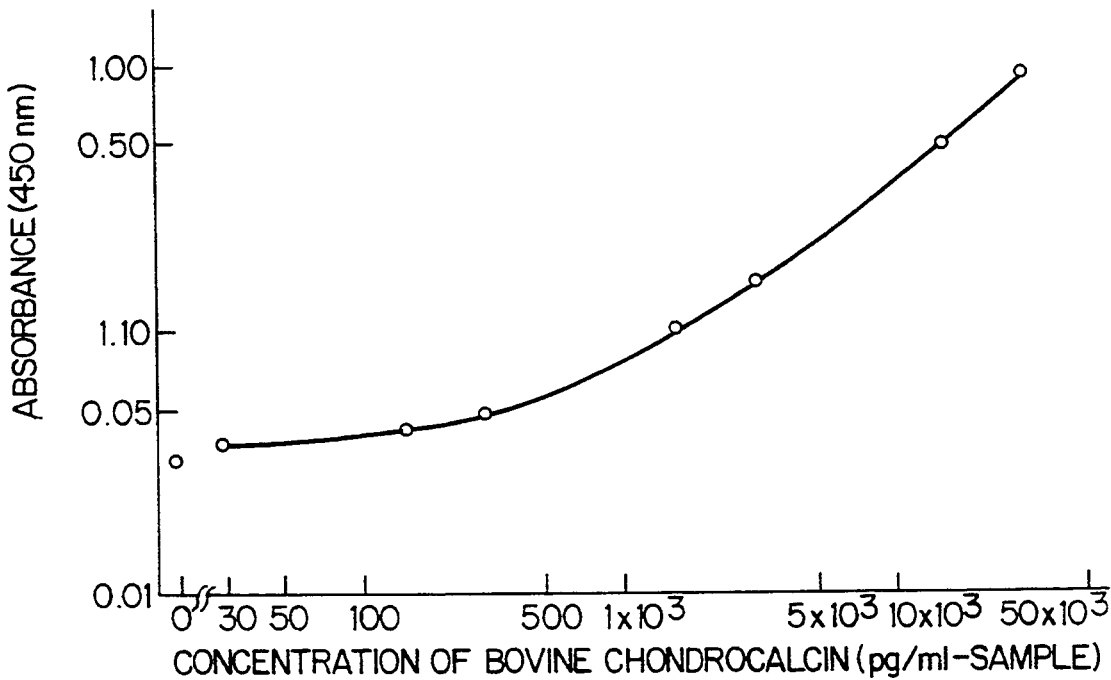
FIG. 10 is a calibration curve for determination of human chondrocalcin in the specimens using anti-bovine-chondrocalcin polyclonal antibody and Fab' of anti-bovine-chondrocalcin polyclonal antibody labeled with peroxidase as reagents.

The bovine chondrocalcin in the dilution series was determined using the polyclonal antibody-immobilized plate and the HRP-labeled Fab' which had been prepared in the same way as in Example 9 to draw the calibration curve in FIG. 10.

Then, a specimen of serum or synovial fluid was combined with 4-fold volume of 1% BSA-final concentration 0.00625% skim milk-PBS (pH 7.2) to prepare the 5-fold diluted specimen. Then, the absorbance was measured as in Example 9 and human chondrocalcin converted from bovine chondrocalcin was calculated from the calibration curve in FIG. 10.

The results are summarized in Table 4.

As shown clearly in the calibration curve in FIG. 10, the lower limit of the measurement according to the present invention is 30 pg/ml and showed markedly higher sensitivity than that of the radioimmunoassay according to A. Hinek et al., of 100 ng/ml lower limit.

TABLE 4

| No. | Diseases | Fluid | Absorbance | Concentration |
| --- | --- | --- | --- | --- |
| 1 | Osteoarthritis | Serum | 0.054 | 450 pg/ml |
| 2 | Osteosarcoma | Serum | 0.086 | 1,300 |
| 3 | Osteoarthritis | Synovial F. | 0.110 | 2,050 |
| 4. | Osteoarthritis | Synovial F. | 0.229 | 6,200 |

EXAMPLE 13

Preparation of peroxidase-labeled anti-chondrocalcin F(ab')$_2$-labeled antibody 1. Preparation of the F(ab')$_2$ fragment of anti-chondrocalcin rabbit polyclonal antibody Pepsin 0.1 mg was added to 2.5 ml of a solution of anti-chondrocalcin rabbit polyclonal antibody described in Example 2 (6.0 mg) in an acetate buffer solution (pH 4.5), they were incubated at 37° C. one overnight, and subjected to HPLC whose pH had been adjusted to 6.0 with 1N NaOH (the column: TSK gel G-3,000SW, the eluent: PBS pH 7.2) to collect 3.6 mg of F(ab')$_2$.

2. Maleimidization of F(ab')$_2$

F(ab')$_2$ fragment (3.6 mg) was dissolved in PBS, and 0.09 ml of a solution of succinimidyl-m-maleimide benzoate (MBS) solution in DMF (10 mg/ml) was added dropwise to the F(ab')$_2$ solution at 25° C. After agitation for 30 minutes, the solution was subjected to column chromatography using a column of 1 cm × 45 cm filled with Sephadex G-25 and 0.1M phosphate buffer solution as an eluent to collect 4.0 mg of maleimidized F(ab')$_2$ fragment.

3. Introduction of the thiol group of peroxidase

An S-acetylmercaptosuccinic anhydride solution in DMF (6.0 mg/ml), 0.2 ml, was gradually added dropwise to 5.4 ml of a peroxidase (Toyo Spinning Co. Ltd.: 54 mg) solution in 0.1M phosphate buffer (pH 6.5) and the reaction was continued for additional 1 hour. The solution was combined with 2.1 ml of 0.1M tris hydrochloric acid buffer (pH 7.0), 0.4 ml of 0.1M EDTA solution and 4.3 ml of 1M hydroxylamine solution, then they were stirred at 30° C. for 5 minutes. The resultant solution was placed in a dialysis tube, and dialyzed against 0.1M phosphate buffer solution (pH 6.0)-5 mM EDTA at 4° C. for two overnights to give a peroxidase solution including SH groups (2.54 mg/ml).

4. Bonding of the maleimidized F(ab')$_2$ fragment to thiol-containing peroxidase.

The maleimidized F(ab')$_2$, 4.0 mg, and the thiol-containing peroxidase solution (2.54 mg/ml), 2.8 ml, mixed and left to stand one overnight at 25° C. The reaction mixture was subjected to HPLC (column: TSK Gel G-3,000SW) using PBS (pH 7.2) as an eluent to collect the fractions of peroxi-dase-bonded F(ab')$_2$ whereby F(ab')2 was obtained by 3.1 mg.

The molar ratio of the F(ab')$_2$ fragment to the peroxidase was 1:2.7 in the fraction.

EXAMPLE 14

Anti-chondrocalcin polyclonal antibody described in Example 2 was dissolved in 0.01M phosphate-buffered physiological saline solution (abbreviated to PBS hereinafter) so that the concentration was adjusted to 20 82 g/ml and mirror-finished polystyrene beads [Immunochemical:immunobeads having 1.3 μm surface center-line average roughness (Ra) measured with Surfcom 570A (Tokyo Precision Co. Ltd.)]were dipped in the solution and allowed to stand at 4° C. for one overnight. The beads were rinsed with PBS 3 times, then allowed to stand in 1% BSA-PBS (pH 7.2) at room temperature for 2 hours. The beads were rinsed again with PBS 3 times, and stored in PBS at 4° C. until they were used.

Solutions of chondrocalcin in 0.75% BSA-0.01% skim milk-PBS (pH 7.2) were prepared, varying the concentrations as follows: 0, 0,025, 0.3125, 0,625, 1.25, 5 ng, and these solutions were placed in small plastic tubes made of polypropylene 0.2 ml each. Then, the peroxide-labeled anti-chondrocalcin F(ab')2 fragment, which was prepared in Example 13, was dissolved in 0.5% BSA-0.2% skim milk-PBS (pH 7.2) so that the concentration became 3 μg/ml as the F(ab')$_2$, and the solution was added to the individual tubes 0.2 ml each. Immediately after addition, the anti-chondrocalcin immobilized beads were added to the tubes one bead each and they were incubated at 37° C. for 90 minutes.

The beads were washed with a solution of PBS containing 0.05% Tween 20 (abbreviated to PBS-T) 3 times, then 2.3 mM hydrogen peroxide-0,025% 3,3', 5,5'-tetramethylbenzidine solution was added to the tubes 0.4 ml each to incubate at 37° C. for 30 minutes. Then, 1 ml of 1N sulfuric acid was added to terminate the color reaction, and the absorbance was determined at 450 nm wavelength.

Figure 11:
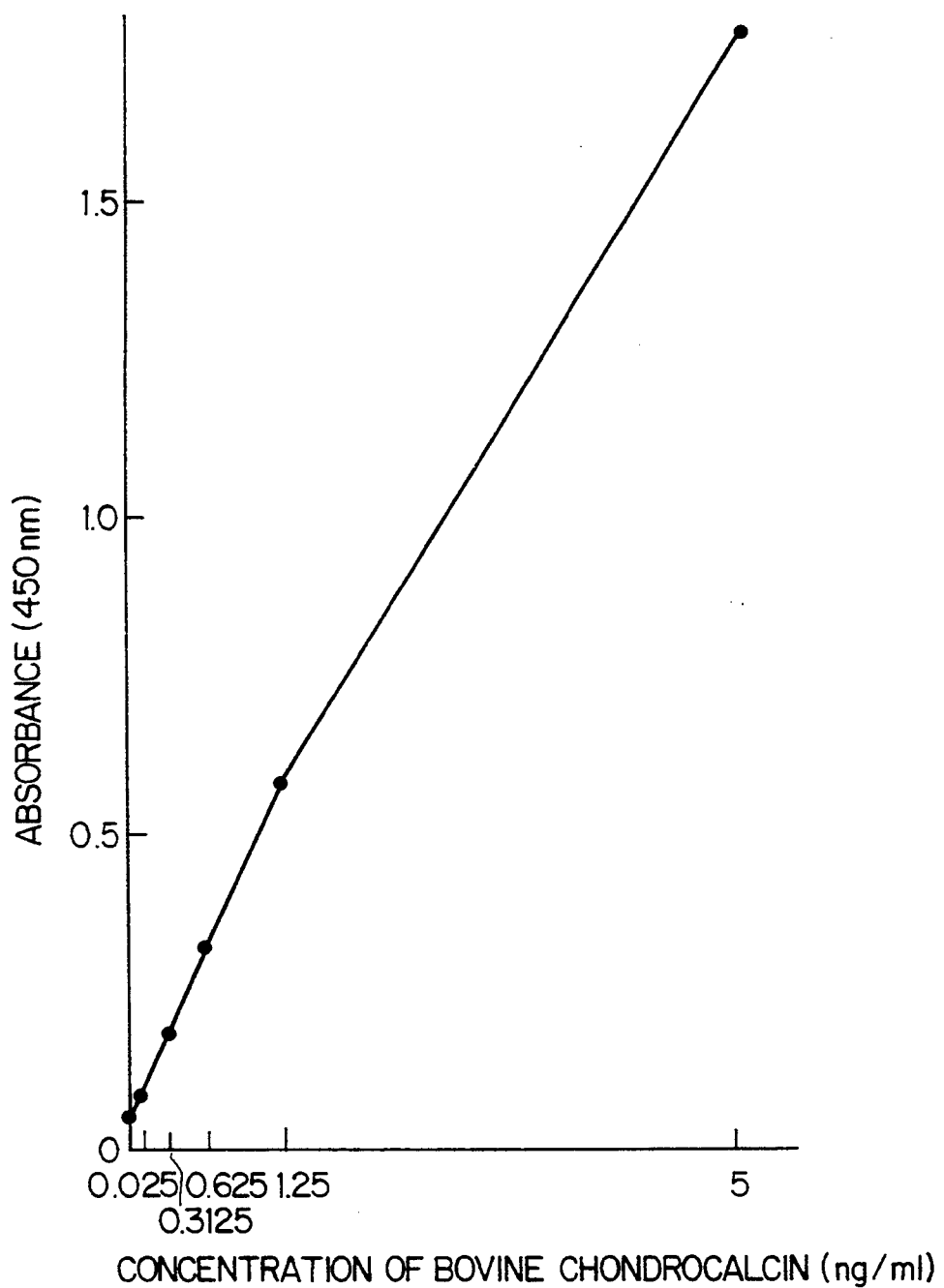
FIG. 11 is a calibration curve for determination of human chondrocalcin in body fluid using anti-bovine-chondrocalcin polyclonal antibody immobilized on mirror-finished polystyrene beads and F(ab')$_2$ of anti-bovine-chondrocalcin antibody labeled with peroxide.

The resultant calibration curve are shown in FIG. 11. The lower limit was 25 pg/ml, and the sensitivity was markedly higher than that in the radioimmunoassay according to A. Hinek et al., 100 ng/ml [see A. Hinek et al., J. Cell. Biol. 104, 1435–1441 (1987)].

Subsequently, specimens of serum or synovial fluid were diluted with 3-fold volume of 0.75% BSA-0.01% skim milk-10 mM PBS (pH 7.2) to prepare 4-fold diluted specimens and their absorbance was measured as in drawing the above calibration curve. Thus, human chondrocalcin converted from bovine chondrocalcin was determined from the calibration curve in FIG. 11.

The results are given in Table 5.

TABLE 5

| No. | Diseases | Fluid | Absorbance | Concentration |
| --- | --- | --- | --- | --- |
| 1 | Osteoarthritis | Synovial F. | 0.580 | 5.0 ng/ml |
| 2 | Osteoarthritis | Synovial F. | 0.775 | 7.1 ng/ml |
| 3 | Osteoarthritis | Synovial F. | 0.310 | 2.4 ng/ml |

TABLE 5-continued

| No. | Diseases | Fluid | Absorbance | Concentration |
|---|---|---|---|---|
| 4 | Osteoarthritis | Synovial F. | 0.395 | 3.4 ng/ml |
| 5 | Osteoarthritis | Synovial F. | 0.325 | 2.5 ng/ml |
| 6 | Osteoarthritis | Synovial F. | 1.005 | 9.9 ng/ml |
| 7 | Osteoarthritis | serum | 0.153 | 0.9 ng/ml |
| 8 | Chronic R. A.* | Synovial F. | 0.085 | 0.2 ng/ml |
| 9 | Chronic R. A. | Synovial F. | 0.090 | 0.3 ng/ml |
| 10 | Chronic R. A. | Synovial F. | 0.105 | 0.5 ng/ml |

Note: *Chronic R. A. = Chronic Rheumatoid Arthritis

We claim:

1. A sandwich immunoassay method for screening for or monitoring the treatment of cartilage diseases in mammals by detecting chondrocalcin in a specimen comprising mammalian body fluid comprising:
   (1) preparing an anti-chondrocalcin antibody immobilized on an insoluble support of mirror-finished beads and an anti-chondrocalcin antibody labeled with at least one enzyme,
   (2) contacting, in solution, the immobilized antibody and the labeled antibody, with the specimen comprising mammalian body fluid, and
   (3) determining the presence of chondrocalcin by detecting the amount of bound labeled anti-chondrocalcin antibody, and
   (4) relating the presence of chondrocalcin to the presence or state of cartilage disease,
   wherein, said solution contains a nonspecific protein having a molecular weight of 16,000 to 50,000 and an isoelectric point of 1.0 to 5.0 or a mixture containing the nonspecific protein is present such that the final concentration of the nonspecific protein is 0.02 to 0.9% by weight.

2. The immunoassay according to claim 1, wherein at least one of the anti-chondrocalcin antibody immobilized on an insoluble support and the labeled anti-chondrocalcin antibody is a monoclonal antibody that specifically binds to human chondrocalcin and which is obtained by a method comprising immunizing an animal with a mammalian chondrocalcin obtained from a different kind of animal.

3. The immunoassay chondrocalcin according to claim 1, wherein at least one of the anti-chondrocalcin antibody immobilized on an insoluble support and the labeled anti-chondrocalcin antibody is a polyclonal antibody that binds to human chondrocalcin and which is obtained by a method comprising immunizing a mammal with chondrocalcin obtained from a different kind of mammal.

4. The immunoassay chondrocalcin according to claim 1, wherein the labeled anti-chondrocalcin antibody is an Fab' fragment or an F(ab')₂ fragment of an anti-chondrocalcin antibody.

5. The immunoassay according to claim 1, wherein the labeled anti-chondrocalcin antibody is an anti-chondrocalcin antibody labeled with 1.5 or more molecules of enzyme per one molecule of the antibody.

6. The immunoassay according to claim 1, wherein the mixture containing the nonspecific protein is skim milk.

7. The immunoassay according to claim 1, wherein the mammalian body fluid is selected from the group consisting of blood in the form of serum or plasma, joint fluid, lymph, thymic fluid, ascitic fluid, amniotic fluid, cell tissue fluid, myeloid fluid and urine.

8. A reagent for screening for monitoring the treatment of cartilage diseases in mammals by immunologically detecting the presence of chondrocalcin in a specimen comprising mammalian body fluid, the reagent comprising an anti-chondrocalcin antibody immobilized on an insoluble support of mirror-finished beads and an anti-chondrocalcin antibody labeled with at least one enzyme, in solution, wherein, a nonspecific protein having a molecular weight of 16,000 to 50,000 and an isoelectric point of 1.0 to 5.0 or a mixture containing the nonspecific protein is present such that the final concentration of the nonspecific protein is 0.02 to 0.9% by weight.

9. The reagent according to claim 8, wherein at least one of the anti-chondrocalcin antibody immobilized on an insoluble support and the labeled anti-chondrocalcin antibody is a monoclonal antibody that specifically binds to human chondrocalcin and which is obtained by a method comprising immunizing an animal with a mammalian chondrocalcin.

10. The reagent according to claim 8, wherein at least one of the anti-chondrocalcin antibody immobilized on an insoluble support and the labeled anti-chondrocalcin antibody is a polyclonal antibody that binds to human chondrocalcin and which is obtained by a method comprising immunizing a mammal with chondrocalcin obtained from a different kind of mammal.

11. The reagent according to claim 8, wherein the labeled anti-chondrocalcin antibody is an Fab' fragment or an F(ab')₂ fragment of an anti-chondrocalcin antibody.

12. The reagent according to claim 8, wherein the labeled anti-chondrocalcin antibody is an anti-chondrocalcin antibody labeled with 1.5 or more molecules of enzyme per one molecule of the antibody.

13. The reagent according to claim 8, wherein the mixture containing the nonspecific protein is skim milk.

14. A kit for screening or monitoring the treatment of cartilage diseases in mammals by immunologically detecting the presence of chrondrocalcin in a specimen comprising mammalian body fluid, the kit comprising an anti-chondrocalcin antibody immunobilized on an insoluble support of mirror-finished beads, an anti-chondrocalcin antibody labeled with at least an enzyme, a solubilizer, a washing agent, a substrate for measuring activity of said at least one enzyme and a reaction terminator therefor, and a nonspecific protein in solution having a molecular weight of 16,000 to 50,000 and an isoelectric point of 1.0 to 5.0 or a mixture containing the nonspecific protein is present such that the final concentration of the nonspecific protein is 0.02 to 0.9% by weight.

15. A sandwich immunoassay method for screening for or monitoring the treatment of cartilage diseases in mammals by detecting chondrocalcin in a specimen comprising mammalian body fluid, said immunoassay method comprising contacting an anti-chondrocalcin antibody immobilized on an insoluble support and an anti-chondrocalcin antibody labelled with at least one enzyme, with said specimen comprising mammalian body fluid, determining the presence of chondrocalcin by detecting the amount of bound labeled anti-chondrocalcin antibody, and relating the presence of chondrocalcin to the presence or state of cartilage disease.

* * * * *